United States Patent [19]

Rapoport

[11] 4,371,474
[45] Feb. 1, 1983

[54] HYDROCYANATION OF OLEFINS

[75] Inventor: Morris Rapoport, Orange, Tex.

[73] Assignee: E. I. Du Pont de Nemours and Company, Wilmington, Del.

[21] Appl. No.: 339,059

[22] Filed: Jan. 13, 1982

[51] Int. Cl.³ ............................................ C07C 120/02
[52] U.S. Cl. ............................................. 260/465.8 R
[58] Field of Search ................................ 260/465.8 R

[56] References Cited

U.S. PATENT DOCUMENTS 3,496,218  2/1970  Drinkard, Jr. ............... 200/465.8 R
3,766,237  10/1973 Chia et al. ................ 260/465.8 R X
3,853,948  12/1974 Drinkard, Jr. et al. .......... 260/465.9
3,903,120  9/1975  Shook, Jr. et al. ......... 252/431 N X Primary Examiner—Joseph P. Brust

[57] ABSTRACT

An improved process for the production of dinitriles, e.g., adiponitrile, by the hydrocyanation of 3- and/or 4-pentenenitriles using a zero-valent nickel complexed with a phosphorus containing ligand as a catalyst with a molar ratio of total ligand to nickel of about 5.0–7.8.

7 Claims, No Drawings

HYDROCYANATION OF OLEFINS

BACKGROUND OF THE INVENTION

1. Field of the Invention

The present process is directed to the production of dinitriles and more particularly, to the production of adiponitrile by the hydrocyanation of 3- and/or 4-pentenenitriles in the presence of a zero-valent nickel catalyst promoted by an organoborane wherein the catalyst efficiency is maximized; the amount of promoter required to sustain a satisfactory reaction is minimized and operation at desirably low temperatures is more readily achieved.

2. Description of the Prior Art

U.S. Pat. No. 3,496,218 issued on Feb. 17, 1970 describes in general terms a process for the preparation of dinitriles especially adiponitrile by the hydrocyanation of non-conjugated, ethylenically unsaturated organic compounds, e.g., 3- and/or 4-pentenenitriles using certain nickel complexes as catalysts. The catalysts are promoted by organoborane compounds such as triphenylborane. A wide range of process conditions and relative amounts and types of reactants are disclosed. In addition, the patentee discloses that at least a two mol excess ligand with respect to the nickel complex can be employed but that there is little advantage in exceeding a 300 molar excess. The use of excess ligand which can be the same or different than the ligand attached to the nickel in the nickel complex is taught to improve product distribution and to extend catalyst life. The minimum amount of ligand exemplified by the patentee using the promoter herein disclosed is approximately 14 mols of total ligand for each mol of zero-valent nickel (14/1) with the majority of examples disclosing about 24/1.

A particularly useful form of zero-valent nickel catalyst is described in U.S. Pat. No. 3,766,237 issued on Oct. 16, 1973. The patentees disclose the use of an excess of the triarylphosphite ligand in the hydrocyanation along with the addition of certain ethers to improve the yield and increase the pounds of product which can be made per pound of catalyst consumed. The patentees teach that at least six and preferably at least 12 mols of total ligand per mol of zero-valent nickel can be employed and exemplify a minimum of 13 using the herein-described promoter.

For a different reaction the use of at least a one and preferably at least a two molar excess of a variety of ligands in a catalyst employed for the isomerization of 2-methyl-3-butenenitrile is disclosed in U.S. Pat. No. 3,853,948 issued on Dec. 10, 1974.

SUMMARY OF THE INVENTION

An improved continuous process for the production of dinitriles (DN's), e.g., adiponitrile by the hydrocyanation of unsaturated nitriles, for example, 3- and/or 4-pentenenitriles in the presence of a zero-valent nickel [Ni(O)] catalyst, represented by formula $NiL_4$ where L is $P(OAr)_3$ and Ar is an aryl group having up to 18 carbon atoms, e.g., tritolylphosphite (TTP) promoted with an arylborane, e.g., triphenylborane (TPB). This process comprises, or consists of, maintaining the temperature of the hydrocyanation at less than about 75° C. and preferably in the range 30°–65° C., the amount of hydrogen cyanide relative to other compounds participating in the reaction such that the overall mol ratio of hydrogen cyanide to the unsaturated nitrile is in the range of about 0.18/1 to 0.7/1, the overall mol ratio of hydrogen cyanide to zero-valent nickel catalyst in the range of about 10/1 to 116/1 and the overall mol ratio of hydrogen cyanide to promoter in the range about 30/1 to 400/1 and further maintaining the molar ratio of total ligand (L) to zero-valent nickel [Ni(O)], L/Ni(O), in the range 5.0–7.8.

In a preferred mode of operation the temperature of the hydrocyanation is in the range 30°–65° C. and the overall mol ratio of hydrogen cyanide to 3- and/or 4-pentenenitriles, to zero-valent nickel catalyst and to promoter is in the range 0.25/1 to 0.55/1; 20/1 to 75/1 and 150/1 to 400/1 respectively and the molar ratio of total ligand to zero-valent nickel is at about 6/1.

DETAILED DESCRIPTION OF THE INVENTION

The present invention can be employed to produce a variety of dinitriles but adiponitrile (ADN) is of particular interest because it is an intermediate used in the production of hexamethylenediamine which in turn is used to produce polyhexamethyleneadipamide, a commercial polyamide useful in forming fibers, films and molded articles.

All ratios referred to herein are molar ratios and the amount of ligand is total ligand unless otherwise specified.

Although the hydrocyanation reaction can employ any non-conjugated, ethylenically unsaturated organic nitrile of from 4 to 20 carbon atoms it is of particular interest in the hydrocyanation of pentenenitriles, e.g., cis- and trans-3-pentenenitrile (3PN), 4-pentenenitrile (4PN) and mixtures thereof (3,4-PN's).

The preparation of zero-valent nickel [Ni(O)] catalyst which is used in the practice of the present invention is found in U.S. Pat. No. 3,903,120 issued on Sept. 2, 1975. Of particular interest is catalyst having the general formula $NiL_4$ where L is a neutral ligand such as a triarylphosphite of the formula $P(OAr)_3$ wherein Ar is an aryl group of up to 18 carbon atoms. Illustrative of the aryl groups are methoxyphenyl, tolyl, xylyl and phenyl. Meta- and para-tolyl and mixtures thereof are the preferred aryl groups.

The art has disclosed that certain advantages can be obtained by the use of more ligand, (L), than is required to form the $NiL_4$ complex. Substantial amounts of ligand are taught to be effective in achieving such advantages e.g., up to 354 mols of ligand for each mol of nickel in the catalyst. The ligand can vary over a wide range e.g., from at least 6 to the aforementioned 354 mols of ligand per mol of nickel. It has now been discovered that the already disclosed benefits of using excess ligand may be retained and additional benefits realized if the ligand is controlled within a very narrow range at or below the lower end of the range of ligand to nickel [L/Ni(O)] previously disclosed so long as other reaction conditions, as discussed below, are maintained.

As one skilled in the art appreciates, an effective catalyst not only yields the desired distribution of products but also assists in the formation of such products at economically attractive rates. It has now been discovered that in order to consistently obtain commercially attractive rates the amount of ligand should be maintained at a ligand to nickel ratio of less than 20/1 e.g., about 9/1. More importantly, it has also been discovered that if the amount of ligand is maintained so that molar ratio of the ligand to zero-valent nickel is in the range of about 5.0–7.8 mols and preferably about 6/1 on the same basis, the catalyst utility can be substantially improved and/or the amount of promoter required for satisfactory continuous operation can be reduced. Unacceptably poor catalyst utility is realized below a molar ratio of ligand to zero-valent nickel of about 5.0 while higher temperatures (higher yield loss) and/or increased promoter loadings are required to sustain the reaction at acceptable rates if the ratio exceeds about 7.8. Since ligand must be recovered and recycled for economical operation, the use of catalysts having a ligand to nickel ratio within the above described range results in less ligand being introduced which, in turn, means that less ligand must be recycled with attendant energy and equipment savings.

The promoters which are used with the above described catalyst are triarylboranes including those of the formula $BR_3$ wherein R is an aryl or substituted aryl group having 6 to 12 carbon atoms, e.g., phenyl, ortho-tolyl, para-tolyl, napthyl, methoxyphenyl, biphenyl, chlorophenyl and bromophenyl. Triphenylborane (TPB) is preferred.

The hydrocyanation can be conducted in one or more steps or stages. If a plurality of stages is employed, it is preferred that the stages be in series with the product from one stage being directed to a subsequent stage. The hydrogen cyanide can be introduced into the first stage or split between stages. It is preferred to conduct the process continuously.

The hydrocyanation must be conducted within certain limits to permit effective use of the zerovalent nickel catalyst with the amount of ligand within the ranges discussed. One limitation is temperature. In order to produce ADN in an acceptable yield at commercially feasible rates the temperature is maintained above 25° C. but less than about 75° C. because at temperatures above 75° C. e.g., 100° C. it has been found that the yield loss is excessive and that no commercially practical adjustments in the reactants or other reaction variables can be made to duplicate performance at lower temperatures. It is preferred to maintain the temperature in the range of 30°–65° C.

Another limitation is in the amount of HCN relative to the other compounds participating in the reaction. As the amount of HCN relative to the 3PN and/or 4PN is increased the conversion of those nitriles increases and their concentration in the reaction products decreases. This results in reduced yield loss. However, the amount of promoter and/or catalyst required to sustain the reaction concurrently increases which adversely affects the economics of the process. Conversely, as the amount of HCN relative to the 3PN and/or 4PN decreases the yield loss increases and the cost of recovering 3PN and/or 4PN increases. By maintaining the ratio of HCN to 3PN and/or 4PN in the range of about 0.18/1 to 0.7/1 and preferably in the range 0.25/1 to 0.55/1 the benefit of improved yield and the detriment of promoter cost and catalyst and 3,4-PN's recovery costs are balanced.

As the ratio of HCN to Ni(O) increases beyond 116/1 the reaction is difficult to sustain unless excessive amounts of promoter are used. Otherwise, higher temperatures are required and the yield loss increases. At ratios below 10/1 even though the reaction is vigorous and the yield loss is small, the cost of recovering the catalyst becomes excessive. The preferred balance is realized at an HCN/Ni(O) ratio in the range 20/1 to 75/1.

The amount of HCN relative to promoter e.g., TPB in the reaction has been found to affect the activity of the catalyst. When the ratio of HCN/promoter exceeds 400/1 the activity of the catalyst decreases to an extent that the temperature of the reaction must be increased beyond that required to obtain an acceptable yield and unless excessive amounts of catalyst are used the yield loss to 2PN is excessive. When the ratio of HCN/promoter decreases below about 25/1 the cost of promoter is excessive. Operation at a ratio of HCN to promoter within the range of about 30/1 to 400/1 and preferably in the range 150/1 to 400/1 permits operation at an acceptable rate and temperature.

The advantages of using a catalyst having a ligand to nickel ratio of 5.0–7.8 are realized when the above variables are maintained as discussed.

The following examples are presented to illustrate but not to restrict the present invention. Parts and percentages are by weight unless otherwise noted. The following abbreviations and definitions are used in the Examples:

TTP = the reaction product of $PCl_3$ and commercially available m,p-cresol which contains minor amounts of related phenols.

$$\text{Conversion} = \frac{\text{mols of 3- and 4-PN's consumed}}{\text{mols of 3- and 4-PN's fed}} \times 100$$

The apparatus employed in all the Examples consisted of 1, 2, or 3 glass flasks as reactors of approximately 25 cc in volume which, when more than one reactor was employed, were connected in series with the overflow from the first reactor directed by gravity to the second reactor and the overflow from the second reactor directed by gravity to the third reactor. Overflow from the last reactor was retained in a product receiver which was periodically changed. Each reactor was equipped with an individually controlled electrical heating means and side arms for sampling the contents during the course of a run. The first reactor was provided with an inlet port for catalyst solution, promoter solution and pentenenitriles. Each reactor was also equipped with a port for introduction of hydrogen cyanide below the liquid contents of the flasks. A nitrogen inlet was provided to the vapor space of each reactor and the product receiver to provide a non-oxidizing atmosphere. The pentenenitriles introduced to the reactor and used to prepare the solutions described hereinbelow contained about 98% 3PN and 1% 4PN with trace amounts of other nitriles. Pentenenitriles of lesser purity can be employed with essentially similar results. Catalyst solution which was introduced into the first reactor was first prepared by reacting a mixture containing 77% TTP, 20% PN's, 3% nickel powder, to which mixture had been added 100 ppm chloride catalyst as phosphorous trichloride. The mixture was heated for 16 hours at 80° C., cooled and filtered to yield a solution containing approximately 2.7% by weight zero-valent nickel [Ni(O)] to which additional ligand was added to obtain the ratio set forth in the Table. The promoter solution was prepared by dissolving a mixture of dry TPB in the above described nitriles to yield a solution containing about 20% by weight triphenylborane. Hydrogen cyanide employed in the examples was essentially free of sulfuric acid and contained only trace amounts of sulfur dioxide. The hydrogen cyanide was cooled to about 0° C. to prevent degradation prior to introduction in the first stage (or stages). The system was started up by adding catalyst solution, pentenenitriles and promoter solution to each reactor at room temperature. Agitation was then started. After warming the reactor(s) to the indicated temperature introduction of hydrogen cyanide was commenced. When the reactor reached steady state as shown by a constant concentration of hydrogen cyanide in the reaction medium at a level indicating substantial reaction of the HCN, samples of the reactor contents and product were withdrawn and analyzed by gas chromatographic analysis to determine the amount of ADN and other dinitriles. The remaining active nickel was analyzed by high pressure liquid chromatography.

The results are reported in the Table.

TABLE

| Example No. | Feed Mol Ratio of HCN To | | | | Feed (wt % Ni(O)) | Conv. (%) | Temp (°C.) | Overall Rate (grams ADN/ cc/min × 10$^4$) | Catalyst Efficiency (Mol Ratio of DN's Made to Ni(O) Consumed) | Mol Ratio of TTP to Ni(O) |
|---|---|---|---|---|---|---|---|---|---|---|
| | Ni(O) | TPB | TTP | 3,4-PN | | | | | | |
| 1 | 50.2 | 98.9 | 9.39 | 0.482 | 0.472 | 50.3 | 50.0 | 11.0 | 275 | 5.35 |
| 2 | 49.1 | 100.7 | 7.94 | 0.483 | 0.484 | 49.7 | 50.0 | 11.0 | 460 | 6.18 |
| 3 | 47.5 | 99.7 | 6.12 | 0.484 | 0.449 | 50.2 | 50.0 | 11.0 | 410 | 7.77 |
| 4 | 38.6 | 168.9 | 5.12 | 0.416$^1$ | 0.489 | 40.6 | 42.9$^{2,3}$ | 5.4 | 320 | 7.54 |
| 5 | 25.1 | 297.8 | 4.07 | 0.395$^4$ | 0.671 | 38.7 | 45.9$^{3,5}$ | 3.6 | 940 | 6.18 |
| C-1 | 26.0 | 258.8 | 3.14 | 0.393$^6$ | 0.598 | 40.2 | 48.7$^{3,7}$ | 3.7 | 440 | 8.27 |
| C-2 | 50.0 | 49.9 | 10.70 | 0.455 | 0.473 | 47.3 | 50.0 | 5.5 | 130 | 4.69 |

$^1$One part of regular 3PN and 4PN feed was combined with about one part of a stream containing about 70% 3PN and 4PN, about 10% 2PN, about 12% 2-methyl-2-butenenitrile and 8% valeronitrile
$^2$HCN fed to two reactors
60.3% to first - 39.7% second
First reactor 35° C. - Second reactor 55° C.
$^3$Weighted Average
$^4$As in Footnote 1, except that one part of regular feed was combined with 2.2 parts of the stream
$^5$HCN fed to three reactors
43% to first - 39% second - 18% third
First reactor 45° C. - Second reactor 45° C. - Third reactor 50° C.
$^6$As in Footnote 1, except that one part of regular feed was combined with 0.85 part of the stream
$^7$HCN fed to three reactors
43% to first - 39% to second - 18% to third
First reactor 45° C. - Second reactor 50° C. - Third reactor 55° C.

Examples 1–5 show that the hydrocyanation can be conducted at satisfactory rates with relatively low levels of promoter and good catalyst utility.

The benefits of the present invention are sharply illustrated when Examples 1–3 are compared with Comparative 2. Stable operation in Comparative 2 was possible only when the production rate was reduced to one half of that in Examples 1–3 and the amount of promoter was doubled. Catalyst utility was poor.

Example 5 should be compared with Comparative 1 which experiments were started under the same conditions except for the TTP/Ni(O) ratio. After about 23 hour the HCN leakage in Comparative 1 had exceeded the level necessary for stable reaction. The temperature was increased in two increments to a weighted average of 48.7° C. over a period of five hours in order to maintain stability. After four hours the reaction had again become unstable and was stabilized at this time by increasing the level of promoter rather than by a further increase in temperature because of potential yield penalty. The final conditions which provided stable operation are shown in the Table. Example 5 required no significant adjustments to achieve stable operation.

I claim:

1. A continuous process for the hydrocyanation of non-conjugated, ethylenically unsaturated organic nitriles having 4 to 20 carbon atoms to produce the corresponding dinitriles which process comprises conducting the hydrocyanation in the presence of a zero-valent nickel ligand-containing catalyst having the general formula NiL$_4$ where L is P(OAr)$_3$ and Ar is an aryl or substituted aryl group having up to 18 carbon atoms promoted with an arylborane, maintaining the temperature of the hydrocyanation at less than about 75° C., controlling the amount of hydrogen cyanide relative to other compounds participating in the reaction such that the overall mol ratio of hydrogen cyanide to unsaturated nitrile is in the range of about 0.18/1 to 0.7/1, the overall mol ratio of hydrogen cyanide to zero-valent nickel catalyst in the range of about 10/1 to 116/1 and the overall mol ratio of hydrogen cyanide to promoter in the range about 30/1 to 400/1 and the molar ratio of total ligand to zero-valent nickel introduced as a catalyst in the range 5.0–7.8.

2. The process of claim 1 wherein the non-conjugated, ethylenically unsaturated nitrile is selected from the class consisting of 3-pentenenitrile, 4-pentenenitrile and mixtures thereof, the mol ratio of hydrogen cyanide to 3- and/or 4-pentenenitriles, zero-valent nickel catalyst and promoter is in the range of 0.25/1 to 0.55/1; 20/1 to 75/1 and 150/1 to 400/1 respectively and wherein the molar ratio of total ligand to nickel is maintained at about 6/1.

3. The process of claims 1 or 2 wherein the arylborane promoter has the formula BR$_3$ where R is an aryl group having 6–12 carbon atoms.

4. The process of claim 3 wherein Ar is selected from the class consisting of meta-tolyl, para-tolyl and mixtures thereof and R is phenyl.

5. The process of claim 1 wherein the molar ratio of total ligand to nickel is about 6/1.

6. The process of claim 4 wherein the molar ratio of total ligand to nickel is about 6/1.

7. The process of claim 2 wherein the temperature is maintained in the range 30°–65° C.

* * * * *